(12) United States Patent
Williams et al.

(10) Patent No.: US 8,931,908 B2
(45) Date of Patent: Jan. 13, 2015

(54) AIR PURGE COLLAR

(75) Inventors: Derek Williams, Santa Cruz, CA (US);
Gary Garnier, Los Gatos, CA (US);
Kent Stemer, Los Gatos, CA (US); Paul Carlson, Santa Cruz, CA (US)

(73) Assignee: Fluke Corporation, Everett, WA (US)

( * ) Notice: Subject to any disclaimer, the term of this patent is extended or adjusted under 35 U.S.C. 154(b) by 1267 days.

(21) Appl. No.: 12/183,647

(22) Filed: Jul. 31, 2008

(65) Prior Publication Data

US 2010/0024887 A1 Feb. 4, 2010

(51) Int. Cl.
*B60R 1/00* (2006.01)
*F15D 1/00* (2006.01)

(52) U.S. Cl.
CPC .................... *F15D 1/00* (2013.01)
USPC ........................................ 359/509

(58) Field of Classification Search
CPC ....... G01J 5/029; G01J 5/043; G01J 27/0006; B60R 1/0602
USPC .......... 137/833, 807, 803; 359/509; 374/125; 454/189, 190
See application file for complete search history.

(56) References Cited

U.S. PATENT DOCUMENTS

| | | | | |
|---|---|---|---|---|
| 3,628,028 A * | 12/1971 | Thorsheim | ............... | 250/576 |
| 3,815,199 A * | 6/1974 | Malavazos | ............... | 29/890.09 |
| 4,240,691 A * | 12/1980 | Holmqvist et al. | ............. | 359/509 |
| 4,277,131 A * | 7/1981 | Hart et al. | ............... | 359/509 |
| 4,521,089 A * | 6/1985 | Bohl et al. | ............... | 359/507 |
| 4,650,318 A * | 3/1987 | Pointer et al. | ............... | 356/43 |
| 4,738,528 A * | 4/1988 | Craft | ............... | 356/43 |
| 4,786,188 A * | 11/1988 | Myhre et al. | ............... | 374/125 |
| 4,836,689 A * | 6/1989 | O'Brien et al. | ............... | 374/125 |
| 5,115,342 A * | 5/1992 | Rowe et al. | ............... | 359/509 |
| 5,146,244 A * | 9/1992 | Myhre et al. | ............... | 359/509 |
| 5,599,105 A * | 2/1997 | Ridley et al. | ............... | 374/125 |
| 6,288,769 B1 * | 9/2001 | Akagawa et al. | ............... | 355/30 |
| 6,538,232 B2 * | 3/2003 | Lambert | ............... | 219/121.84 |
| 6,890,080 B2 * | 5/2005 | Kalley et al. | ............... | 359/509 |
| 7,128,427 B2 * | 10/2006 | Van Peski et al. | ............... | 359/509 |
| 7,138,640 B1 * | 11/2006 | Delgado et al. | ............... | 250/372 |
| 7,319,524 B2 * | 1/2008 | Friedrichs | ............... | 356/438 |
| 7,522,834 B2 * | 4/2009 | Heaven et al. | ............... | 396/535 |
| 2002/0109826 A1 * | 8/2002 | Akagawa et al. | ............... | 355/53 |
| 2003/0142403 A1 * | 7/2003 | Kalley et al. | ............... | 359/509 |
| 2003/0197909 A1 * | 10/2003 | Beyer et al. | ............... | 359/196 |
| 2003/0210906 A1 * | 11/2003 | Peterson et al. | ............... | 396/427 |
| 2007/0103780 A1 * | 5/2007 | Cooper | ............... | 359/509 |
| 2007/0206942 A1 * | 9/2007 | Gyde Heaven et al. | ............... | 396/287 |
| 2007/0229954 A1 * | 10/2007 | Bral | ............... | 359/509 |

* cited by examiner

*Primary Examiner* — Alexander Comley
(74) *Attorney, Agent, or Firm* — Christensen O'Connor Johnson Kindness PLLC

(57) ABSTRACT

An air purge apparatus and method is presented to protect an imaging system from contamination by particulate matter and other substances in the ambient environment. The apparatus is adapted to be placed adjacent to a viewing window, lens or optics of an imaging system and to provide a protective flow of air. The apparatus includes a curved surface to direct air from a first plenum toward an imaging path in front of the apparatus. The apparatus also includes one or more openings nearer the lens to direct air from a second plenum into the imaging path. The air from the first plenum entrains air from the second plenum and ambient air to create a fluid stream away from the viewing window, lens, or optics and may form a fluid barrier to reduce contamination of a volume of air in the imaging path of the imaging sensor.

25 Claims, 7 Drawing Sheets

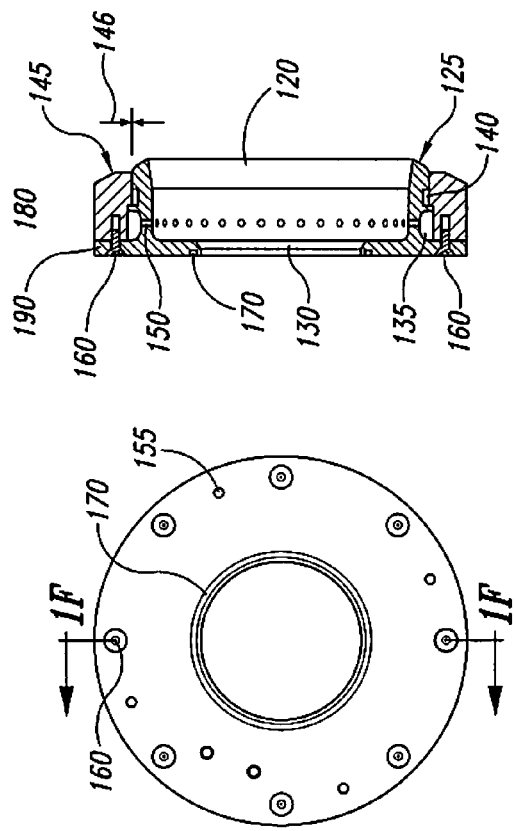

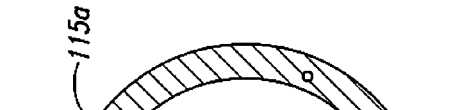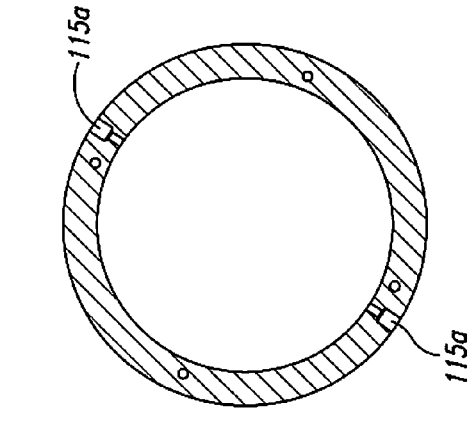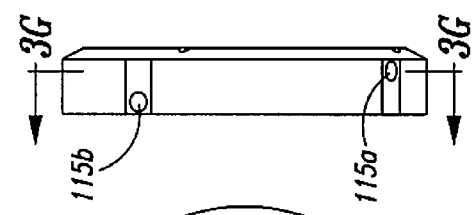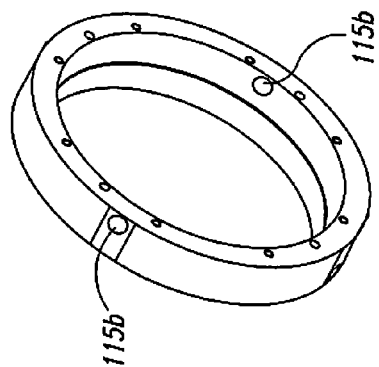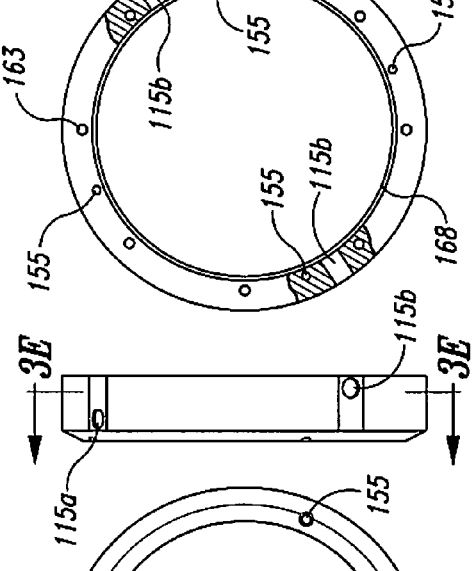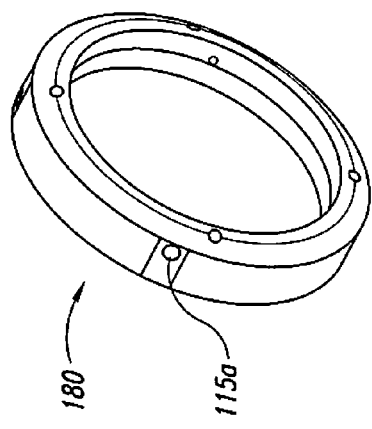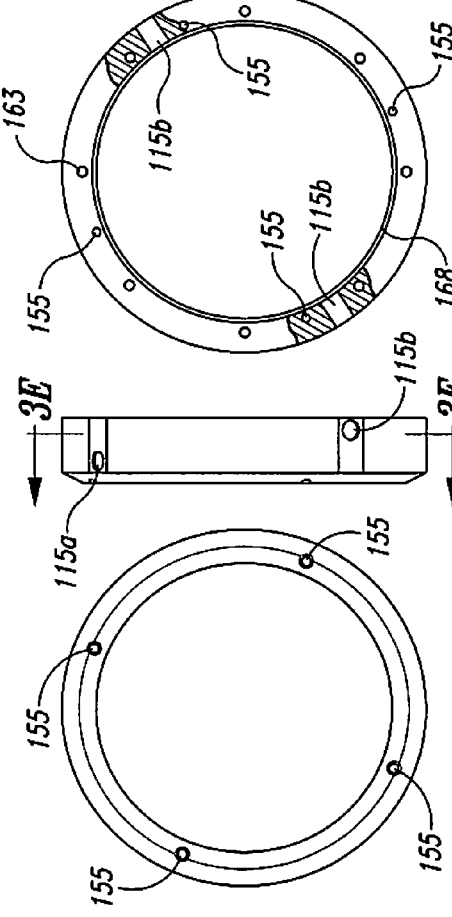

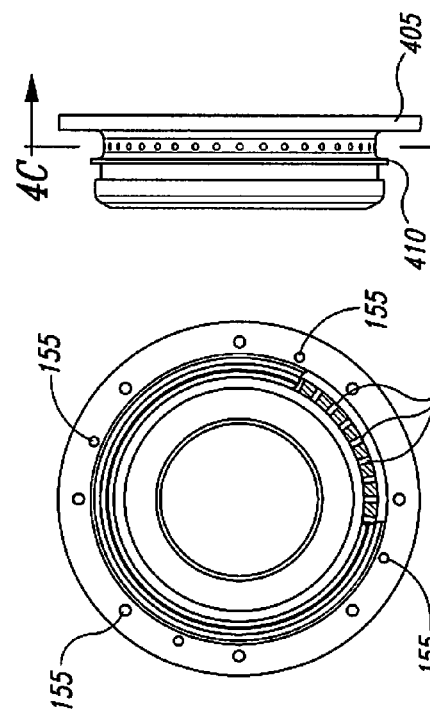
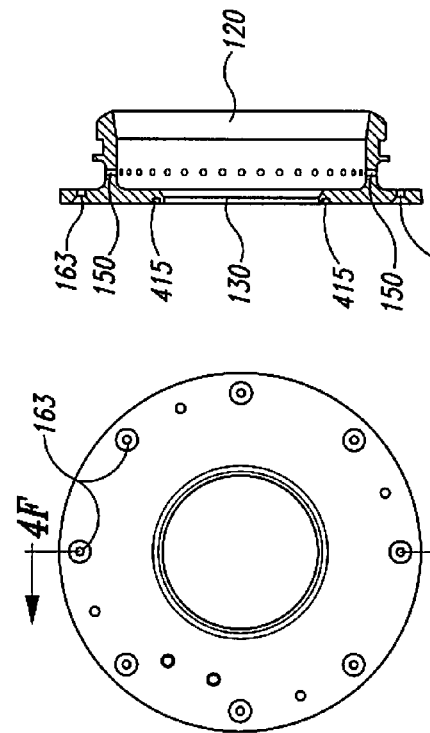
Fig. 4A
Fig. 4B
Fig. 4C
Fig. 4D
Fig. 4E
Fig. 4F

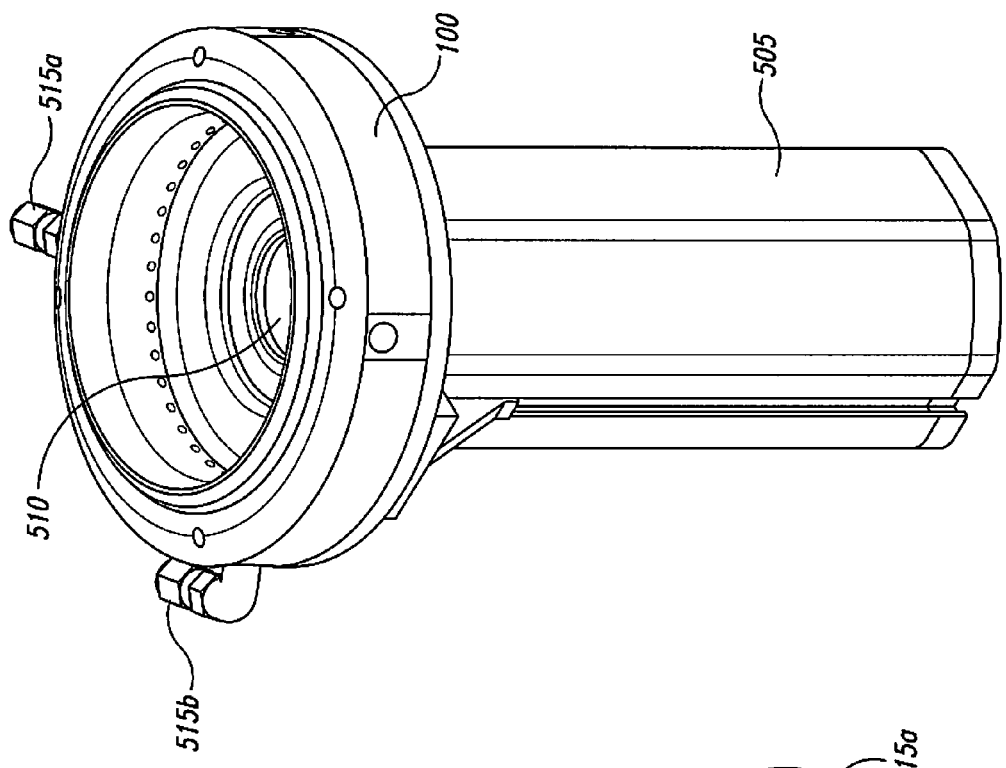
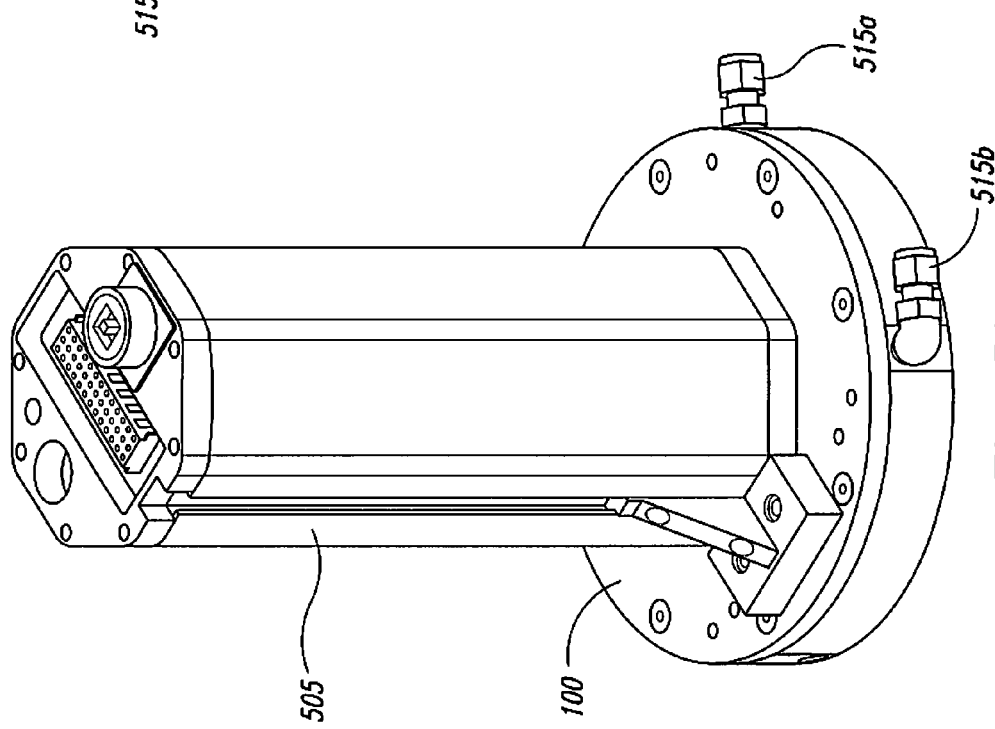

AIR PURGE COLLAR

FIELD OF THE INVENTION

The following is related to methods and apparatus for air purging imaging systems. More particularly, the following is related to air purging employed to protect an imaging system lens from contamination.

BACKGROUND

Air purge systems have traditionally been employed to protect particular surfaces or areas from various hazards present in the surrounding environment. For example, the air in a factory may include airborne droplets of oil, water or other fluids, dirt, dust, manufacturing scraps, metallic particles, and/or a variety of other particulates. In such an environment, an air purge system may be useful, e.g., to prevent particulates from interfering with the function of an imaging system. Such particulates may interfere with optical imaging systems, infrared or other thermal imaging systems, laser systems, x-ray systems, ultrasonic systems, and/or the like.

To accomplish this objective, traditional air purge systems may employ a tube, shroud, or other conduit that blows clean dry air near the particular surface or area. For instance, an imaging system often requires a clear view of the object or area of interest, and an associated air purge system may include one or more tubes that continually blows clean, dry air past a viewing window or lens of the imaging system. Such blowing may push contaminants in the ambient air away from the viewing window or lens and thereby prevent dirt or other particulates from contacting or adhering to the viewing window of the imaging system.

In one application, a housing or tube may extend outwardly from the lens or viewing window and enable clean dry air to be introduced such that ambient air is pushed away from the lens. However, housings and tubes of this type may limit the field of view, cause vignetting in wide field of view applications, or provide insufficient isolation or protection of the imaging system from the ambient air. For example, some air purge systems employing tubes may generate turbulent air flow in the vicinity of the imaging system viewing window or lens and fail to provide consistent protection from contaminants over the entire area or surface for which protection is sought.

The increasing use of imaging applications in a variety of settings has resulted in increased demand for wider field of view imaging products, such as thermal imaging products. Infrared and other thermal imaging systems typically use a wide field of view, resulting in relatively large optical components, lenses, or protective viewing windows. In addition, combined optical/thermal imaging systems may include an integrated visible light camera as well as a thermal imager to provide a fused visible/thermal image, which increases the size of the optical components even further and correspondingly increases the size of the area or surface for which protection from contaminants is sought. There is thus a need for improved air purge systems capable of protecting larger areas and surfaces from contamination in a consistent and effective manner.

SUMMARY OF THE INVENTION

An improved air purge system, apparatus and method is presented which solves the aforementioned problems and others by providing a primary air flow and a secondary air flow to protect a viewing window, lens, or optics of an imaging sensor from contamination by particulate matter and other substances in the ambient environment. The apparatus is adapted to be placed adjacent to a viewing window, lens or optics of an imaging system and to provide a protective flow of air. The apparatus includes a curved surface to direct a primary airflow from a first plenum toward an imaging path in front of the apparatus. The apparatus also includes one or more openings nearer the lens to direct a secondary airflow from a second plenum into the imaging path. The primary airflow from the first plenum entrains at least a portion of the secondary airflow from the second plenum and ambient air to create a fluid stream away from the viewing window, lens, or optics and may form a fluid barrier to reduce contamination of a volume of air in the imaging path of the imaging sensor.

In one aspect, a fluid purge apparatus is provided including a collar having an upstream collar opening and a downstream collar opening, the collar substantially encircling a protected volume to be purged; at least one primary flow pathway formed in the collar and configured to provide a primary fluid stream adjacent a curved surface positioned to encourage attached flow of the primary fluid stream over at least a portion of the curved surface adjacent the downstream collar opening; at least one secondary flow pathway formed in the collar and configured to provide a secondary fluid stream adjacent the upstream collar opening; whereby the primary flow pathway is positioned relative to the secondary flow pathway such that the primary fluid stream entrains the secondary fluid stream to purge the protected volume.

In another aspect, a method of purging air from a protected volume in an imaging path of an imaging sensor includes receiving air from one or more air sources to establish a primary airflow and a secondary airflow, directing the secondary airflow into the protected volume upstream of the primary airflow, directing the primary airflow near a curved surface such that the primary airflow is attached along at least a portion of the curved surface and the primary airflow flows downstream and nearby the secondary airflow, whereby the primary airflow entrains at least a portion of the secondary airflow such that a fluid stream flows within the protected volume in the imaging path in a downstream direction generally away from the imaging sensor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified. The below drawings are not necessarily drawn to scale.

FIG. 1A is an isometric front view of an embodiment of an air purge collar according to aspects of the invention;

FIG. 1B is an isometric rear view of the air purge collar of FIG. 1A;

FIG. 1C is a front plan view of the air purge collar of FIG. 1A;

FIG. 1D is a side view of the air purge collar of FIG. 1A;

FIG. 1E is a rear plan view of the air purge collar of FIG. 1A;

FIG. 1F is a partial cross-section view of the air purge collar of FIG. 1A along line A-A of FIG. 1E;

FIG. 3A is an isometric front view of an embodiment of an air purge collar case according to aspects of the invention;

FIG. 3B is an isometric rear view of the air purge collar case of FIG. 3A;

FIG. 3C is a front plan view of the air purge collar case of FIG. 3A;

FIG. 3D is a right side view of the air purge collar case of FIG. 3A;

FIG. 3E is a partial cross-section view of the air purge collar case of FIG. 3A along line C-C of FIG. 3D;

FIG. 3F is a left side view of the air purge collar case of FIG. 3A;

FIG. 3G is a cross-section view of the air purge collar case of FIG. 3A along line B-B of FIG. 3F;

FIG. 4A is an isometric front view of an embodiment of an air purge collar core according to aspects of the invention;

FIG. 4B is an isometric rear view of the air purge collar core of FIG. 4A;

FIG. 4C is a partial cross-section front view of the air purge collar core of FIG. 4A along line B-B of FIG. 4D;

FIG. 4D is a right side view of the air purge collar core of FIG. 4A;

FIG. 4E is a rear plan view of the air purge collar core of FIG. 4A;

FIG. 4F is partial cross-section view of the air purge collar core of FIG. 4A along line A-A of FIG. 4E;

FIG. 5A is an isometric view illustrating an embodiment of an air purge collar attached to a thermal imager;

FIG. 5B is another isometric view illustrating the air purge collar attached to a thermal imager depicted in FIG. 5A.

DETAILED DESCRIPTION

Figure 1G:
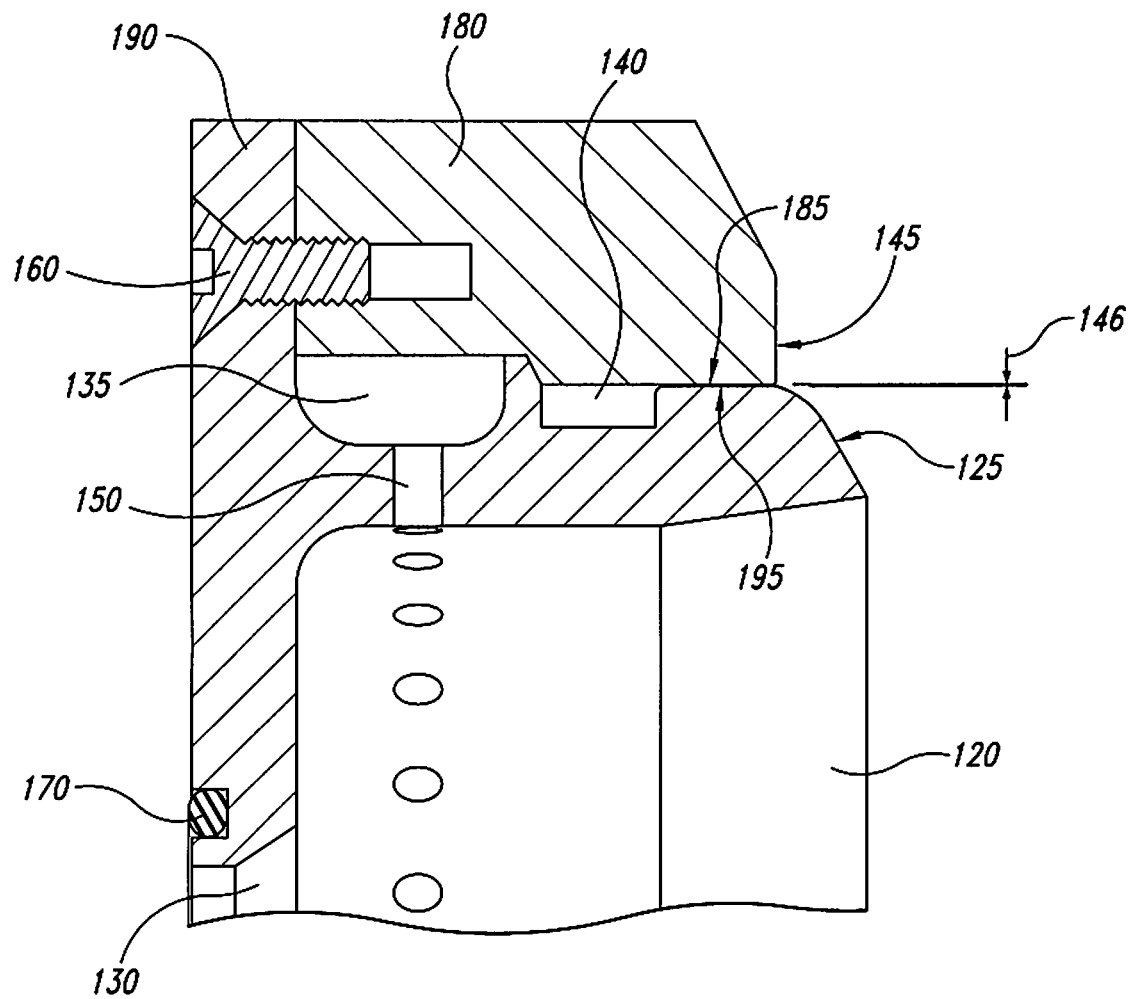
FIG. 1G is an enlarged view of a portion of FIG. 1F.

The following disclosure describes several embodiments of the invention. Several details describing well-known structures or processes are not set forth in the following description for purposes of brevity and clarity. Also, several other embodiments of the invention can have different configurations, components, or procedures than those described in this Detailed Description. A person of ordinary skill in the art, therefore, will accordingly understand that the invention may have other embodiments with additional elements, or the invention may have other embodiments without several of the elements shown and described below with reference to the figures.

An air purge collar is described that provides improved air purging capabilities. The improved air purging capabilities may be employed to provide a protected area or volume near an imaging sensor and to prevent surface contamination of a viewing window, lens, or other optics of an imaging sensor, while simultaneously reducing interference with the imaging sensor's field of view. For example, the improved air purge collar may be employed to improve the performance of thermal imaging sensors by reducing or preventing airborne particulates from contacting a relatively large viewing window (e.g., up to about 6 inches in diameter), thereby preventing or reducing particulate interference with the sensor's imaging function.

Embodiments of the invention may be employed in conjunction with imaging sensors to enable image sensing in dirty environments, in wet environments, in environments with airborne particulates, and/or the like. Embodiments of the invention may also be employed with optical imaging sensors, thermal imaging sensors, laser sensors, x-ray sensors, ultrasonic sensors, and/or the like. Embodiments of the invention may be used in systems employing these and a variety of other sensors known in the art.

An air purge collar may be configured to receive air from one or more air sources. Received air may be employed to reduce or avoid the presence of contaminated ambient air in the vicinity of the imaging sensor optics such that airborne particulates are kept away from the imaging sensor viewing window, lens, or optics. In this way, surface contamination of the imaging sensor viewing window, lens, or optics may be reduced and the performance of the imaging sensor may be improved.

Some embodiments of the invention also describe air purge collars having reduced thickness. For example, such air purge collars may be employed with wide field of view (e.g. greater than 40 degrees) imaging sensors, and the reduced thickness of such embodiments may correspondingly reduce interference at the peripheral boundaries of the wide field of view. Embodiments of the invention also describe air purge collars that are configured to provide two air flows for entraining ambient air and reducing contaminants in the imaging path.

A first (primary) airflow is provided at a front end of the air purge collar near a curved surface. This primary airflow takes advantage of the Coanda effect such that as this primary airflow passes along the curved surface, it tends to remain attached to that surface and flows radially inward and forward of the air purge collar. A secondary airflow is provided nearer the rear end of the air purge collar and is directed into the imaging path. The secondary airflow entrains, or is entrained by, the primary airflow and flows generally away from the imaging sensor, clearing at least a portion of the imaging path of contaminants and reducing or avoiding the presence of ambient air (potentially including contaminants) near the imaging sensor viewing surface, lens, or optics.

In one embodiment, the combination of the primary airflow and the secondary airflow substantially reduces or prevents the flow of ambient air in a protected volume within or near the imaging path of the imaging sensor, including a volume surrounded by the air purge collar and a volume forward of the air purge collar.

FIGS. 1A-1G illustrate air purge collar 100. Air purge collar 100 may be formed from case 180 and core 190. As illustrated, air purge collar 100 includes air inlets 115a-b, forward opening 120, curved surface 125, rear opening 130, first plenum 140, second plenum 135, primary airflow gap 145, secondary airflow conduits 150, o-ring 170, mounting holes 155, and screws 160. Air purge collar 100 provides collared imaging path 165 between rear opening 130 and forward opening 120.

Referring to FIG. 1G, air purge collar 100 includes primary airflow gap 145 including an annular spacing 146 between an upper gap boundary 185 formed in case 180 and a lower gap boundary 195 formed in core 190. The primary airflow gap 145 extends from first plenum 140 to the outside environment to permit a primary airflow 205 (see FIG. 2) through the annular spacing 146. The lower gap boundary 195 and the curved surface 125 may be a substantially continuous surface formed in core 190. Air purge collar 100 further includes secondary airflow conduits 150 formed in core 190 and extending between the second plenum 135 and the outside environment. The secondary airflow conduits 150 terminate in holes 151 formed in core 190 to permit a secondary airflow 210 (see FIG. 2) to flow from the second plenum 135 to a volume of air near or within the imaging path and substantially surrounded by the air purge collar 100.

The primary airflow gap 145 is configured to provide air from first plenum 140 through annular spacing 146 over curved surface 125 to a region in front of air purge collar 100.

In one embodiment, air is provided via primary airflow gap 145 to an area directly in front of air purge collar 100 within or near imaging path 165. In this embodiment, primary airflow gap 145 is a single continuous ring-shaped gap extending around the front end of the air purge collar 100 and the collared imaging path 165. For example, the width of such a gap may be between approximately 0.005 and 0.015 inches, and is preferably about 0.005 inches. However, in alternate embodiments primary airflow gap 145 may include a plurality of openings configured to establish primary airflow 205 near curved surface 125. For example, some embodiments may include multiple openings that are evenly spaced around the front end of air purge collar 100 and adjacent curved surface 125.

The secondary airflow conduits 150 are configured to provide air from second plenum 135 to a region substantially surrounded by air purge collar 100 and within or near imaging path 165. In this embodiment, secondary airflow conduits 150 include forty (40) conduits formed in air purge collar 100 and terminating in holes 151 that are approximately evenly spaced around an inner annular surface of core 190. However, this configuration is not necessary and alternate embodiments may employ other configurations such as a single continuous gap similar to that employed for primary airflow gap 145. In addition, alternate embodiments need not employ secondary airflow conduits positioned to direct secondary airflow 210 perpendicular to imaging path 165, and instead secondary airflow conduits 150 may be configured to direct the secondary airflow 210 so that it has a velocity component along the imaging path 165, e.g. in a downstream direction toward forward opening 120.

Curved surface 125 is configured to assist in directing the primary airflow 205. Making use of the Coanda effect (the tendency of a fluidic flow near an adjacent curved surface to follow that curved surface and thereby "turn" the fluid flow's direction), the primary airflow 205 flowing through primary airflow gap 145 preferably tends to follow the curvature of curved surface 125 and thus primary airflow 205 includes a component of flow radially inward relative to the air purge collar 100 in addition to its axial component in a direction generally away from the rear opening 130. The curvature of curved surface 125 may be selected based on an anticipated air pressure, mass flow rate, volume flow rate, air temperature, air density, and other environmental or engineering factors known in the art. Further, the surface characteristics of curved surface 125 may be selected to establish or maintain particular flow conditions, such as laminar flow, along at least a portion of curved surface extending from primary airflow gap 145. For example, curved surface 125 may be polished to reduce its friction characteristics (e.g. skin friction) relative to air flowing near curved surface 125. For another example, curved surface 125 may be lacquered, painted, electroplated, and/or otherwise treated or formed to encourage favorable flow conditions well known in the art, such as extending attachment, reducing separation, or encouraging re-attachment along at least a portion of curved surface 125.

In one embodiment, collared imaging path 165 between rear opening 130 and forward opening 120 provides an imaging path substantially free of contaminants for improved operation of an imaging sensor. For example, collared imaging path 165 may be substantially cylindrical and forward and rear openings 120, 130 may have a diameter such that air purge collar 100 does not limit the field of view of an associated imaging sensor located adjacent o-ring 170 (see, e.g., FIGS. 5A, 5B showing an exemplary imaging sensor with air purge collar attachment). In this embodiment, air purge collar 100 is configured to protect a region in the imaging path substantially surrounded by the air purge collar 100 as well as the region in front of the forward opening 120.

Figure 2:
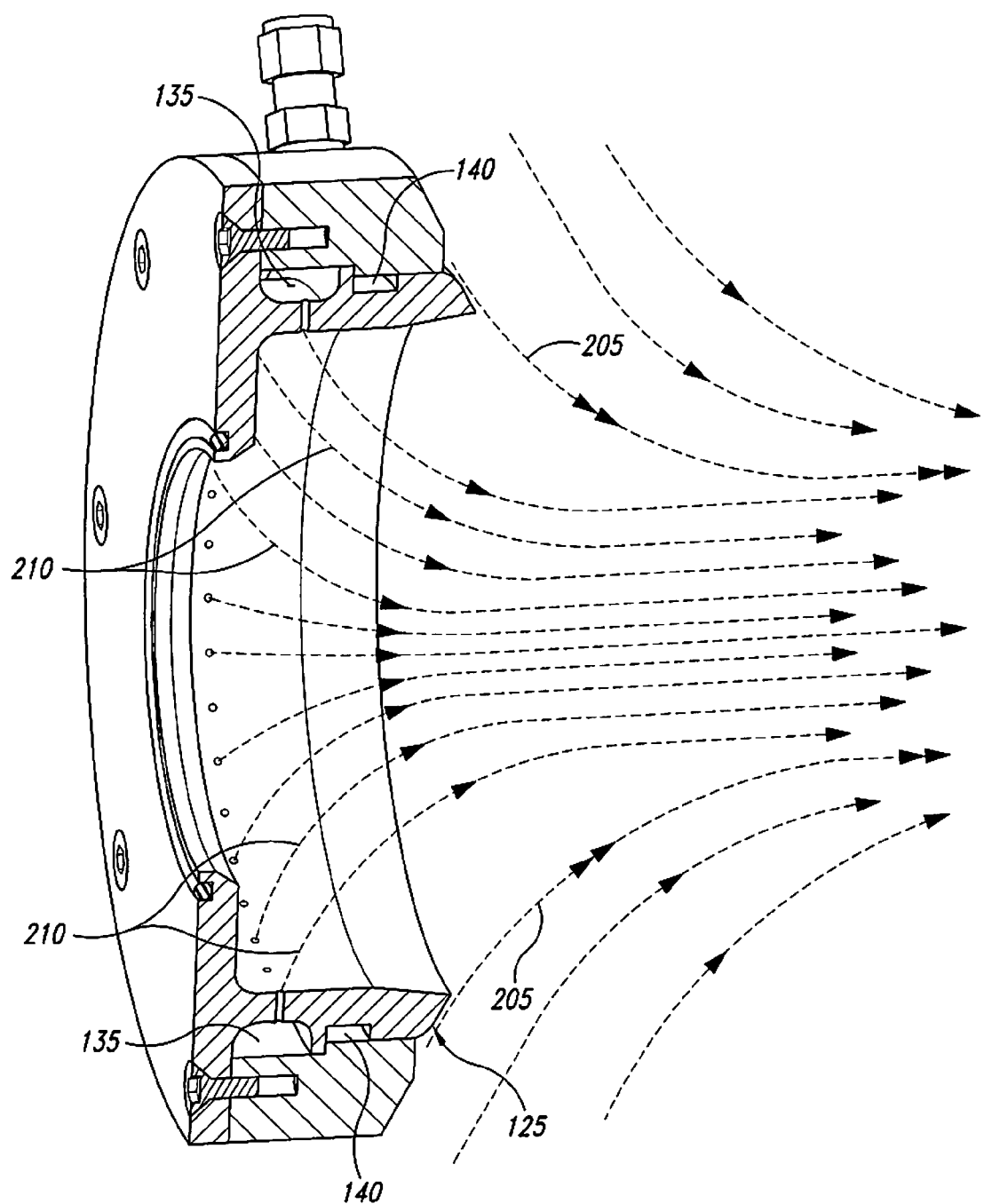
FIG. 2 is an annotated partial isometric view of an embodiment of an air purge collar illustrating operational aspects of the invention.

FIG. 2 illustrates a method embodiment of the invention. FIG. 2 shows a partial isometric view of the air purge collar 100 in operation. This method embodiment includes supplying dry clean air to first plenum 140 to establish primary airflow 205, supplying dry clean air to second plenum 135 to establish secondary airflow 210, maintaining a primary airflow 205 such that primary airflow 205 remains attached to the curved surface 125 as it flows outward from primary airflow gap 145, maintaining a flow rate ratio between primary airflow 205 and secondary airflow 210 such that primary airflow 205 entrains at least a portion of secondary airflow 210, whereby a concentration of contaminants in a volume of air near a forward end of the collar 100 is substantially reduced. The flow rate ratio between primary airflow 205 and secondary airflow 210 may satisfactorily be greater than about 2:1 and is preferably about 3:1 for an exemplary embodiment of the air purge collar 100. However, as would be immediately appreciated by a person of ordinary skill in the art, this ratio may vary for particular implementations of air purge collar 100 according to geometry, pressure, temperature, and humidity of the ambient air, as well as pressure, temperature, and humidity of the supply air, as well as a variety of characteristics of the surrounding environment and potentially contaminated ambient air.

Air inlets 115a-b may be configured to receive air from one or more air sources. In the embodiment illustrated in FIGS. 1A-G and FIG. 2, air inlets 115a may be configured to receive air from a first plurality of air sources to establish the primary airflow 205, and air inlets 115b may be configured to receive air from a second plurality of air sources to establish the secondary airflow 210. However, other embodiments may employ a variety of other air supply configurations known in the art. For example, alternate embodiments may employ only a single first air source via a single air inlet 115a to fill first plenum 140 for primary airflow 205. In addition or alternatively to such an example, a single second air source via a single second air inlet 115b may be used to fill second plenum 135 in support of secondary airflow 210. In alternate embodiments, primary airflow 205 and secondary airflow 210 may be varied via baffles, flow control devices, varying the size and/or configuration of plenums 135, 140, primary airflow gap 145, secondary airflow conduits 150, or other methods known in the art.

In one embodiment, the supplying of dry clean air may be accomplished using a supply of compressed air that has been filtered, and/or dried and cleaned to substantially remove moisture and/or oils that may be present. For example, air inlets 115a-b may receive air from air sources such as air compressors. Such received air may be preferably filtered and/or dried such that oil, water, and other airborne particulates are at least partially removed. However, as a skilled artisan would appreciate, other sources of air may be employed in connection with embodiments of the invention to provide air and/or other gases to air inlets 115a-b.

FIGS. 3A-G show a series of views of an air purge collar case 180 in accordance with an embodiment of the invention. FIGS. 4A-G show a similar series of views of an air purge collar core 190 in accordance with this embodiment. The air purge collar case 180 (FIGS. 3A-G) and the air purge collar core 190 (FIGS. 4A-G) may be assembled together to form an air purge collar 100 (FIGS. 1A-G).

FIGS. 3A and 3B show front and rear isometric views, respectively, of air purge collar case 180. FIGS. 3C and 3E are generally front and rear plan views of case 180, although FIG. 3E includes a partial cross-section view taken along line C-C of FIG. 3D. FIGS. 3D and 3F are right and left side views, respectively, of case 180. FIG. 3G is a cross-section view taken along line B-B of FIG. 3F. The air purge collar case 180 has a generally annular shape and has a number of apertures formed therein including air inlets 115a-b, mounting holes 155, and assembly holes 163 configured to accommodate screws 160 for attachment to core 190. The air purge collar case 180 may include bumper 168 to aid in positioning during attachment to core 190.

FIGS. 4A and 4B show front and rear isometric views, respectively, of air purge collar core 190. FIGS. 4C and 4E are generally front and rear plan views of core 190, although FIG. 4C includes a partial cross-section view taken along lone B-B of FIG. 4D. FIG. 4D is a side view of core 190 and FIG. 4F is a cross-section view taken along line A-A of FIG. 4E. The air purge collar core 190 has a generally annular shape and has a number of apertures formed therein including mounting holes 155, assembly holes 163 configured to accommodate screws 160 for attachment to case 180. The air purge collar core 190 may include flange 410 to aid in positioning during attachment to case 180. Flange 410 also serves to separate first and second plenums 140, 135 when assembled with case 180 in air purge collar 100. Core 190 includes back lip 405 which serves as the rear base of air purge collar 100 when core 190 is assembled with case 180 and includes annular detent 415 formed in its rear-facing surface to accommodate o-ring 170 (see FIG. 2).

FIGS. 5A and 5B illustrate an exemplary embodiment of an air purge collar 100 in accordance with aspects of the invention attached to a thermal imager 505. A front viewing window 510 of the thermal imager 505 is positioned immediately adjacent a rear-facing surface of the air purge collar 100 (e.g. attached with thermal imager 505 pressed against o-ring 170) to protect viewing window 510 from contamination from particulates, etc. in the ambient air. Air supply attachments 515a and 515b may be used to attach air sources to provide clean dry air for primary airflow 205 and secondary airflow 210, respectively. Together with thermal imager 505, air purge collar 100 forms a system and associated method for resisting contamination and improving imaging function.

Figure 6:
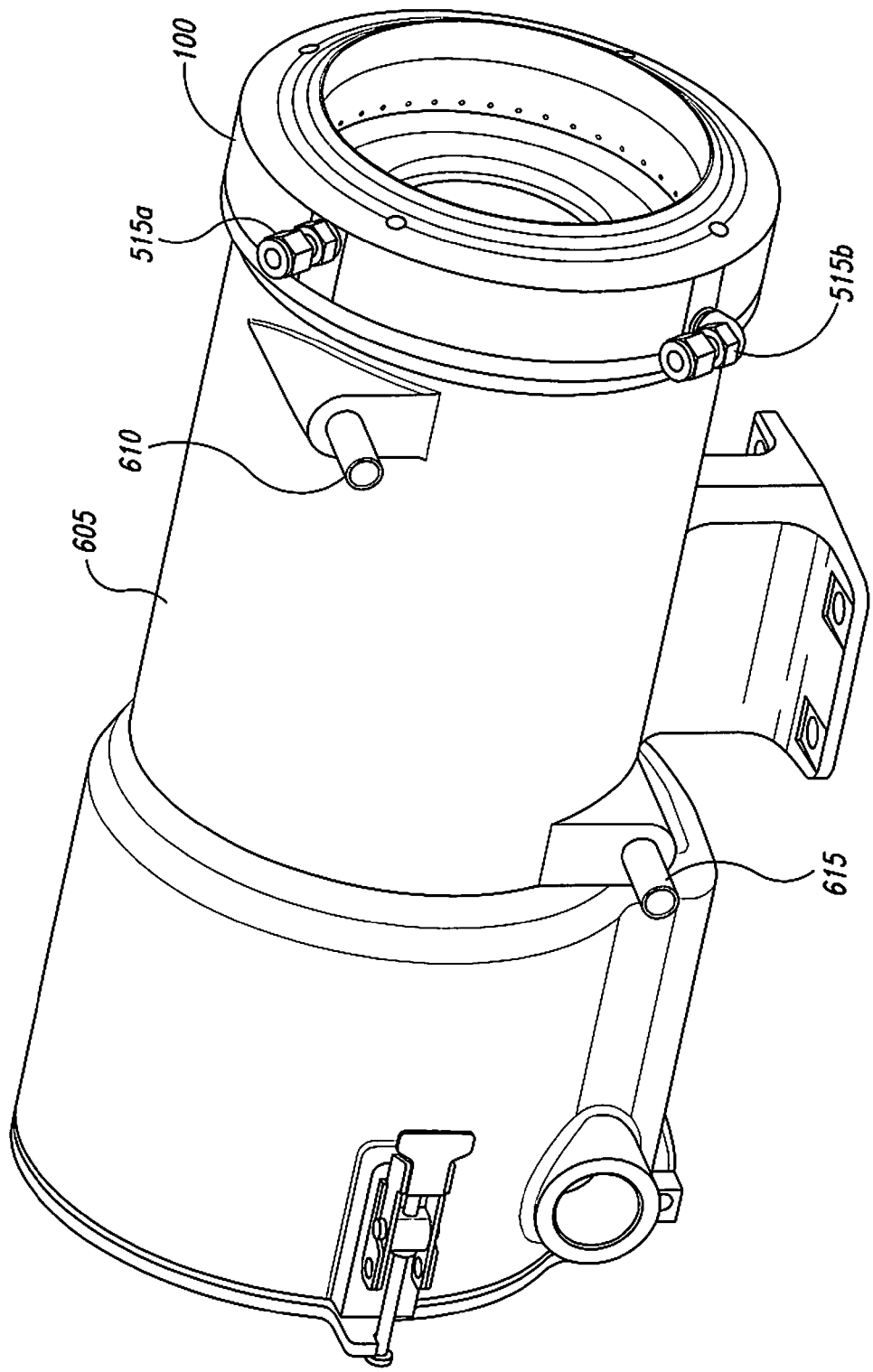
FIG. 6 is an isometric view illustrating an embodiment of an air purge collar attached to an imager within a water cooling jacket.

FIG. 6 illustrates another exemplary embodiment of an air purge collar 100 in accordance with aspects of the invention attached to an imaging instrument within a water cooling jacket 605. For example, in some industrial environments, the ambient air temperature may be insufficiently cool to permit satisfactory operation of an imaging instrument in the absence of an auxiliary cooling system. Water cooling jacket 605 may provide such an auxiliary cooling system including water intake 610, water outlet 615, and at least one heat exchanger (not shown). Air supply attachments 515a and 515b may be used to attach air sources to provide clean dry air for primary airflow 205 and secondary airflow 210, respectively. Together with water cooling jacket 605, air purge collar 100 forms a system and associated method for enhancing instrument cooling, resisting contamination and improving imaging function.

While the above description describes certain embodiments of the invention, and describes the best mode contemplated, no matter how detailed the above appears in text, the invention can be practiced in many ways. Details of the system may vary in implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

We claim:

1. A fluid purge apparatus, comprising: a collar, said collar substantially surrounding a protected volume to be purged, wherein the protected volume has an upstream opening and a downstream opening, and wherein a curved surface is positioned around a periphery of the downstream opening out of the protected volume and the curved surface is defined by a distally decreasing exterior diameter; at least one primary flow pathway formed in the collar and configured to provide a primary fluid stream adjacent the curved surface to encourage attached flow of the primary fluid stream over at least a portion of the curved surface; and at least one secondary flow pathway formed in the collar and configured to provide a secondary fluid stream into the protected volume upstream opening, wherein the secondary flow pathway provides the secondary fluid stream evenly distributed entering around the protected volume upstream opening, and the secondary flow pathway discharges the secondary fluid stream into the protected volume upstream from a location where the primary flow pathway discharges the primary fluid stream to the curved surface; whereby the primary flow pathway is positioned relative to the secondary flow pathway such that an entraining primary fluid stream entrains the secondary fluid stream downstream from the protected volume, wherein the entraining primary fluid stream downstream of the protected volume is a greater amount of flow than the secondary fluid stream.

2. The apparatus of claim 1, wherein the curved surface is configured to encourage the primary fluid stream to flow radially inward of the at least one primary flow pathway.

3. The apparatus of claim 2, wherein the curved surface is configured to employ a Coanda effect to encourage the primary fluid stream to flow radially inward toward the protected volume.

4. The apparatus of claim 1, wherein one or both of the primary fluid stream and the secondary fluid stream include air that has been filtered and dried.

5. The apparatus of claim 1, wherein the protected volume is within a field of view of an imaging instrument.

6. The apparatus of claim 5, wherein the imaging instrument includes a thermal imager.

7. The apparatus of claim 5, wherein the imaging instrument includes a visible light camera.

8. The apparatus of claim 5, wherein the field of view of the imaging instrument is greater than about 40 degrees.

9. The apparatus of claim 5, wherein the imaging instrument includes a viewing window up to about 6 inches in diameter.

10. The apparatus of claim 1, wherein the primary flow pathway comprises a substantially continuous ring-shaped gap extending substantially around the collar in fluid connection with a first plenum.

11. The apparatus of claim 10, wherein the secondary flow pathway comprises a plurality of conduits in fluid connection with a second plenum, the plurality of conduits being radially arranged to provide the secondary fluid stream within a portion of the protected volume enclosed by the collar.

12. The apparatus of claim 11, wherein a ratio of a primary volume flow rate of the primary fluid stream to a secondary volume flow rate of the secondary fluid stream is about 3:1.

13. The apparatus of claim 1, wherein the collar includes a case and a core disposed in the case, wherein the core is attached to the case, and wherein the core is disposed in the case so as to define a first plenum and a second plenum therebetween.

14. A method of purging air from a protected volume in an imaging path of an imaging sensor, comprising:
receiving air from one or more air sources to discharge a primary airflow and a secondary airflow from a collar;

discharging the secondary airflow into an upstream opening of the protected volume upstream of a location where the primary airflow discharges to a curved surface, wherein the secondary airflow is evenly distributed entering around the protected volume upstream opening, and wherein the protected volume is within a field of view of the imaging sensor; and discharging the primary airflow near the curved surface such that the primary airflow is attached along at least a portion of the curved surface, wherein the curved surface is positioned around a periphery of a downstream opening out of the protected volume and the curved surface is defined by a distally decreasing exterior diameter;

whereby an entraining primary airflow entrains at least a portion of the secondary airflow downstream from the protected volume such that a fluid stream flows within the protected volume in the imaging path in a downstream direction generally away from the imaging sensor, wherein the entraining primary airflow downstream of the protected volume is a greater amount of flow than the secondary airflow.

15. The method of claim 14, wherein a ratio of a primary volume flow rate of the primary airflow to a secondary volume flow rate of the secondary airflow is about 3:1.

16. The method of claim 14, wherein the primary airflow, the secondary airflow, and the fluid stream entrain ambient air to establish a fluid barrier that reduces a presence of ambient contaminants within the protected volume in the imaging path.

17. The method of claim 14, wherein the imaging sensor includes a viewing surface, and the primary airflow, the secondary airflow, and the fluid stream entrain ambient air to establish a fluid barrier that reduces contamination of the viewing surface.

18. The method of claim 14, wherein receiving air from one or more air sources includes receiving air from a first plurality of sources to establish the primary airflow and receiving air from a second plurality of sources to establish the secondary airflow.

19. The method of claim 14, wherein receiving air from one or more air sources comprises: receiving air from a single source; and separating the received air into a first plenum and a second plenum, wherein the received air in the first plenum is employed to establish the primary airflow and the received air in the second plenum is employed to establish the secondary airflow.

20. The method of claim 14, wherein discharging the secondary airflow into an upstream opening of the protected volume includes directing the secondary airflow with a velocity component in a downstream direction generally away from the imaging sensor.

21. The method of claim 14, wherein the primary airflow includes a substantially laminar airflow over at least a portion of the curved surface.

22. The method of claim 14, wherein discharging the primary airflow near the curved surface makes use of a Coanda effect to direct the primary airflow toward a point along an optical axis in the imaging path of the imaging sensor.

23. An apparatus for purging air from a protected volume in an imaging path of an imaging sensor, comprising: first means for receiving air from one or more air sources to discharge a primary airflow and a secondary airflow from a collar; second means for discharging the secondary airflow into an upstream opening of the protected volume upstream of a location where the primary airflow discharges to a curved surface, wherein the second means provides the secondary airflow evenly distributed entering around the protected volume upstream opening, and wherein the protected volume is within a field of view of the imaging sensor; and third means for discharging the primary airflow near the curved surface such that the primary airflow is attached along at least a portion of the curved surface and the primary airflow flows downstream from and nearby the secondary airflow, wherein the curved surface is positioned around a periphery of a downstream opening out of the protected volume and the curved surface is defined by a distally decreasing exterior diameter; whereby the second means and third means are configured such that an entraining primary airflow entrains at least a portion of the secondary airflow downstream from the protected volume such that a fluid stream flows within the protected volume in the imaging path in a downstream direction generally away from the imaging sensor, wherein the entraining primary airflow downstream of the protected volume is a greater amount of flow than the secondary airflow.

24. The apparatus of claim 23, further comprising: the collar including the first means, the second means, and the third means; and fourth means for attaching the collar to the imaging sensor.

25. The apparatus of claim 23, wherein the primary airflow includes a substantially laminar airflow over at least a portion of the curved surface.

* * * * *